(12) United States Patent
Al-Mahmood

(10) Patent No.: US 8,828,959 B2
(45) Date of Patent: *Sep. 9, 2014

(54) ANTISENSE OLIGONUCLEOTIDES CAPABLE OF INHIBITING THE FORMATION OF CAPILLARY TUBES BY ENDOTHELIAL CELLS

(75) Inventor: Salman Al-Mahmood, Paris (FR)

(73) Assignee: Gene Signal International SA, Epalinges (CH)

( * ) Notice: Subject to any disclaimer, the term of this patent is extended or adjusted under 35 U.S.C. 154(b) by 952 days.

This patent is subject to a terminal disclaimer.

(21) Appl. No.: 12/050,586

(22) Filed: Mar. 18, 2008

(65) Prior Publication Data

US 2008/0293658 A1   Nov. 27, 2008

Related U.S. Application Data

(60) Division of application No. 10/735,512, filed on Dec. 12, 2003, now Pat. No. 7,417,033, which is a continuation of application No. PCT/FR02/02067, filed on Jun. 14, 2002.

(30) Foreign Application Priority Data

Jun. 14, 2001   (FR) ..................................... 01 07805

(51) Int. Cl.
```
A61K 31/70     (2006.01)
C07H 21/02     (2006.01)
C07H 21/04     (2006.01)
C12N 15/113    (2010.01)
C12Q 1/68      (2006.01)
A61K 31/711    (2006.01)
A61K 38/00     (2006.01)
```

(52) U.S. Cl.
CPC ............ *C12N 15/113* (2013.01); *A61K 31/711* (2013.01); *A61K 38/00* (2013.01); *C12N 2310/11* (2013.01)

USPC ......... 514/44 A; 435/375; 435/377; 536/23.1; 536/24.1; 536/24.5

(58) Field of Classification Search
None
See application file for complete search history.

(56) References Cited

FOREIGN PATENT DOCUMENTS

| EP | 1 010 433 A1 | 6/2000 |
| WO | WO 92/13083 | 8/1992 |
| WO | WO 96/35791 | 11/1996 |

OTHER PUBLICATIONS

Milligan et al., Journal of Medicinal Chemistry, vol. 36(14):1923-1937, 1993.*
Consuelo D'Ambrosio, Susanne R. Keller, Andrea Morrione, Gustav E. Lienhard, Renato Baserga, and Ewa Surmacz, Transforming Potential of the Insulin Receptor Substrate 1, Cell Growth & Differentiation vol. 6, 557-562, May 1995.
William C. Wallace, Candan A. Akar, W.E. Lyons, Hemanta K. Kole, Josephine M. Egan, and Ben Wolozin, Amyloid Precursor Protein Requires the Insulin Signaling Pathway for Neurotrophic Activity, Molecular Brain Research 2 (1997) 213-227.
Ewa Surmacz et al., *Overexpression of Insulin Receptor Substrate 1 (IRS-1) in the Human Breast Cancer Cell Line MCF-7 Induces Loss of Estrogen Requirements for Growth and Transformation*, Clinical Cancer Research, vol. 1, No. 11, Nov. 1995, pp. 1429-1436.

* cited by examiner

*Primary Examiner* — Sean McGarry
(74) *Attorney, Agent, or Firm* — Young & Thompson

(57) ABSTRACT

A pharmaceutical composition that blocks angiogenesis comprising as active agent at least one substance selected from the group consisting of (i) a nucleic acid molecule of a gene coding for protein IRS-1, a complementary sequence or a fragment thereof and (ii) a molecule which inhibits expression of a nucleic acid molecule according to (i).

4 Claims, 5 Drawing Sheets

Subconjunctival injections
of antisense oligonucleotides
(60 μM)

Subconjunctival injections
of sense oligonucleotides
(60 μM)

Topical applications of
antisense oligonucleotide
(200 μM)

Topical applications of
sense oligonucleotide
(200 μM)

No treatment

Subconjunctival injections
of PBS

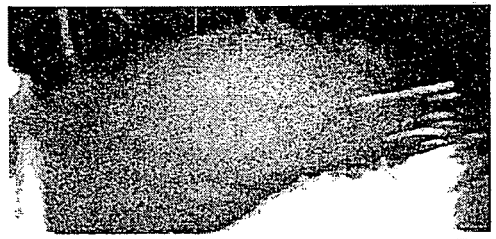
Day 4 AS [antisense] 60    FIG.5A
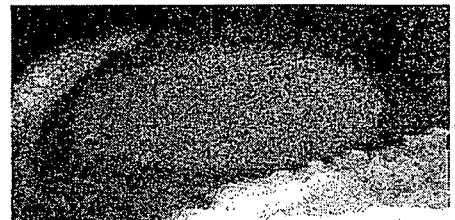
Day 9 AS [antisense] 60    FIG.5F
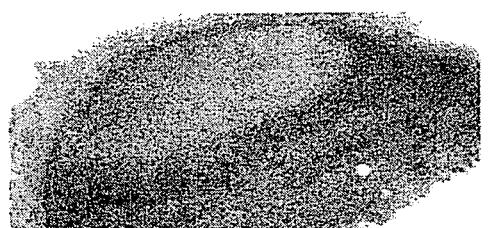
Day 4 AS [antisense] 200    FIG.5B
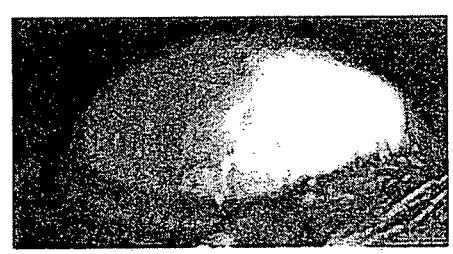
Day 9 AS [antisense] 200    FIG.5G
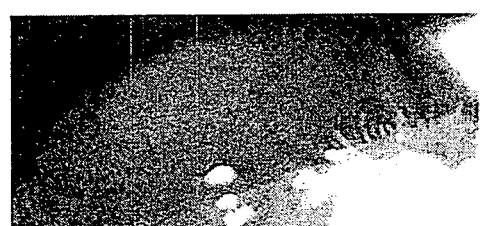
Day 4 S [sense] 200    FIG.5C
Day 9 S [sense] 200    FIG.5H
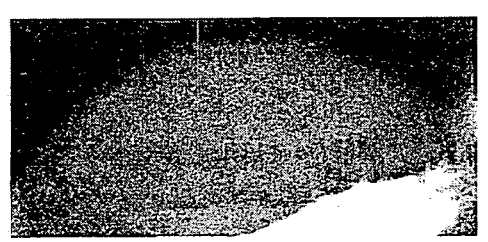
Day 4 PBS    FIG.5D
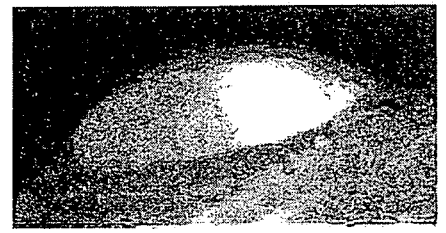
Day 9 PBS    FIG.5I
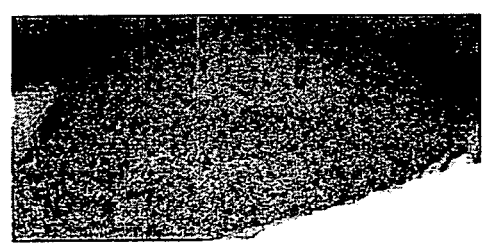
Day 4 No treatment    FIG.5E
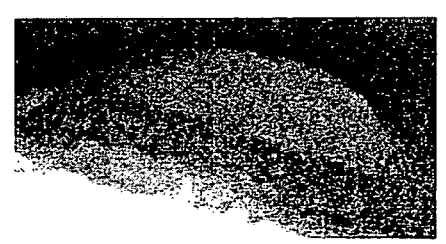
Day 9 No treatment    FIG.5J

SEQUENCE LISTING

<160> NUMBER OF SEQ ID NOS: 30

<210> SEQ ID NO 1
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
tcgatgtgac gctactgatg agtccgtgag gacgaaactc tggcctag          48

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 2
tatccggagg gctcgccatg ctgctgcgga gcaga          35

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 3
tatccggagg gctcgccatg ctgct          25

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 4
tcgccatgct gctgcggagc aga          23

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 5
tatccggagg gcctgccatg ctgct          25

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 6
tatccggagg gcctgccatg ctgc          24

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tatccggagg gcctgccatg ctg                                            23

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tatccggagg gcctgccatg ct                                             22

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tatccggagg gcctgccatg c                                              21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tatccggagg gcctgccatg                                                20

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tatccggagg gcctgccat                                                 19

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tatccggagg gcctgcca                                                  18

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tatccggagg gcctgcc                                                    17

<210> SEQ ID NO 14
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tatccggagg gcctgc                                                     16

<210> SEQ ID NO 15
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tatccggagg gcctg                                                      15

<210> SEQ ID NO 16
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tatccggagg gcct                                                       14

<210> SEQ ID NO 17
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tatccggagg gcc                                                        13

<210> SEQ ID NO 18
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tatccggagg gc                                                         12

```
<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ccggagggcc tgccatgctg ct                                                  22

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gagggcctgc catgctgct                                                      19

<210> SEQ ID NO 21
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ggcctgccat gctgct                                                         16

<210> SEQ ID NO 22
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ctgccatgct gct                                                            13

<210> SEQ ID NO 23
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
tgccatgctg ct                                                             12

<210> SEQ ID NO 24
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tttttttttt ttgg                                                           14

<210> SEQ ID NO 25
```

```
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25 ttttttttt ttag                                                         14

<210> SEQ ID NO 26
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26 ttttttttt ttcg                                                         14

<210> SEQ ID NO 27
<211> LENGTH: 326
<212> TYPE: DNA
<213> ORGANISM: Homo sapiens

<400> SEQUENCE: 27
gtgccgagct gagttcctta taagaattaa tcttaatttt gtattttttc ctgtaagaca       60
ataggccatg ttaattaaac tgaagaagga tatatttggc tgggtgtttt caaatgtcag      120
cttaaaattg gtaattgaat ggaagcaaaa ttataagaag aggaaattaa agtcttccat      180
tgcatgtatt gtaaacagaa ggagatgggt gattccttca attcaaaagc tctctttgga      240
atgaacaatg tgggcgtttg taaattctgg aaatgtcttt ctattcataa taaactagat      300
actgttgatc ttttaaaaaa aaaaaa                                           326

<210> SEQ ID NO 28
<211> LENGTH: 5800
<212> TYPE: DNA
<213> ORGANISM: Homo sapiens
<220> FEATURE:
<221> NAME/KEY: CDS
<222> LOCATION: (1022)..(4747)

<400> SEQUENCE: 28
cggcggcgcg gtcggagggg gccggcgcgc agagccagac gccgccgctt gttttggttg       60
gggctctcgg caactctccg aggaggagga ggaggaggga ggaggggaga agtaactgca      120
gcggcagcgc ctcccgagga acaggcgtct tccccgaacc cttcccaaac ctcccccatc      180
ccctctcgcc cttgtcccct ccctcctcc ccagccgcct ggagcgaggg gcagggatga       240
gtctgtccct ccggccggtc cccagctgca gtggctgccc ggtatcgttt cgcatggaaa      300
agccactttc tccacccgcc gagatgggcc cggatggggg ctgcagagga cgcgcccgcg      360
ggcggcggca gcagcagcag cagcagcagc agcaacagca acagccgcag cgccgcggtc      420
tctgcgactg agctggtatt tgggcggctg gtggcggctg ggacggttgg ggggtgggag      480
gaggcgaagg aggagggaga accccgtgca acgttggac ttggcaaccc gcctccccct       540
gcccaaggat atttaatttg cctcgggaat cgctgcttcc agaggggaac tcaggaggga      600
aggcgcgcgc gcgcgcgcgc tcctggaggg gcaccgcagg gaccccgac tgtcgcctcc       660 ctgtgccgga ctccagccgg ggcgacgaga gatgcatctt cgctccttcc tggtggcggc      720
```

```
ggcggctgag aggagacttg gctctcggag gatcggggct gccctcaccc cggacgcact    780
gcctccccgc cgggcgtgaa gcgcccgaaa actccggtcg ggctctctcc tgggctcagc    840
agctgcgtcc tccttcagct gccccctcccc ggcgcggggg gcggcgtgga tttcagagtc   900
ggggtttctg ctgcctccag ccctgtttgc atgtgccggg ccgcggcgag gagcctccgc    960
cccccacccg gttgttttc ggagcctccc tctgctcagc gttggtggtg gcggtggcag   1020
```

| | |
|---|---|
| c atg gcg agc cct ccg gag agc gat ggc ttc tcg gac gtg cgc aag gtg<br>   Met Ala Ser Pro Pro Glu Ser Asp Gly Phe Ser Asp Val Arg Lys Val<br>    1           5                10              15 | 1069 |
| ggc tac ctg cgc aaa ccc aag agc atg cac aaa cgc ttc ttc gta ctg<br>Gly Tyr Leu Arg Lys Pro Lys Ser Met His Lys Arg Phe Phe Val Leu<br>            20              25             30 | 1117 |
| cgc gcg gcc agc gag gct ggg ggc ccg gcg cgc ctc gag tac tac gag<br>Arg Ala Ala Ser Glu Ala Gly Gly Pro Ala Arg Leu Glu Tyr Tyr Glu<br>       35              40             45 | 1165 |
| aac gag aag aag tgg cgg cac aag tcg agc gcc ccc aaa cgc tcg atc<br>Asn Glu Lys Lys Trp Arg His Lys Ser Ser Ala Pro Lys Arg Ser Ile<br>      50             55            60 | 1213 |
| ccc ctt gag agc tgc ttc aac atc aac aag cgg gct gac tcc aag aac<br>Pro Leu Glu Ser Cys Phe Asn Ile Asn Lys Arg Ala Asp Ser Lys Asn<br> 65             70            75            80 | 1261 |
| aag cac ctg gtg gct ctc tac acc cgg gac gag cac ttt gcc atc gcg<br>Lys His Leu Val Ala Leu Tyr Thr Arg Asp Glu His Phe Ala Ile Ala<br>          85              90             95 | 1309 |
| gcg gac agc gag gcc gag caa gac agc tgg tac cag gct ctc cta cag<br>Ala Asp Ser Glu Ala Glu Gln Asp Ser Trp Tyr Gln Ala Leu Leu Gln<br>            100            105           110 | 1357 |
| ctg cac aac cgt gct aag ggc cac cac gac gga gct gcg gcc ctc ggg<br>Leu His Asn Arg Ala Lys Gly His His Asp Gly Ala Ala Ala Leu Gly<br>      115            120           125 | 1405 |
| gcg gga ggt ggt ggg ggc agc tgc agc ggc agc tcc ggc ctt ggt gag<br>Ala Gly Gly Gly Gly Gly Ser Cys Ser Gly Ser Ser Gly Leu Gly Glu<br>   130               135           140 | 1453 |
| gct ggg gag gac ttg agc tac ggt gac gtg ccc cca gga ccc gca ttc<br>Ala Gly Glu Asp Leu Ser Tyr Gly Asp Val Pro Pro Gly Pro Ala Phe<br>145               150             155             160 | 1501 |
| aaa gag gtc tgg caa gtg atc ctg aag ccc aag ggc ctg ggt cag aca<br>Lys Glu Val Trp Gln Val Ile Leu Lys Pro Lys Gly Leu Gly Gln Thr<br>               165            170           175 | 1549 |
| aag aac ctg att ggt atc tac cgc ctt tgc ctg acc agc aag acc atc<br>Lys Asn Leu Ile Gly Ile Tyr Arg Leu Cys Leu Thr Ser Lys Thr Ile<br>           180             185           190 | 1597 |
| agc ttc gtg aag ctg aac tcg gag gca gcg gcc gtg gtg ctg cag ctg<br>Ser Phe Val Lys Leu Asn Ser Glu Ala Ala Ala Val Val Leu Gln Leu<br>       195             200            205 | 1645 |
| atg aac atc agg cgc tgt ggc cac tcg gaa aac ttc ttc ttc atc gag<br>Met Asn Ile Arg Arg Cys Gly His Ser Glu Asn Phe Phe Phe Ile Glu<br>   210               215            220 | 1693 |
| gtg ggc cgt tct gcc gtg acg ggg ccc ggg gag ttc tgg atg cag gtg<br>Val Gly Arg Ser Ala Val Thr Gly Pro Gly Glu Phe Trp Met Gln Val<br>225               230             235             240 | 1741 |
| gat gac tct gtg gtg gcc cag aac atg cac gag acc atc ctg gag gcc<br>Asp Asp Ser Val Val Ala Gln Asn Met His Glu Thr Ile Leu Glu Ala<br>               245            250            255 | 1789 |
| atg cgg gcc atg agt gat gag ttc cgc cct cgc agc aag agc cag tcc<br>Met Arg Ala Met Ser Asp Glu Phe Arg Pro Arg Ser Lys Ser Gln Ser<br>          260            265            270 | 1837 |
| tcg tcc aac tgc tct aac ccc atc agc gtc ccc ctg cgc cgg cac cat | 1885 |

```
                                                       -continued

Ser Ser Asn Cys Ser Asn Pro Ile Ser Val Pro Leu Arg Arg His His
        275                 280                 285 ctc aac aat ccc ccg ccc agc cag gtg ggg ctg acc cgc cga tca cgc         1933
Leu Asn Asn Pro Pro Pro Ser Gln Val Gly Leu Thr Arg Arg Ser Arg
        290                 295                 300 act gag agc atc acc gcc acc tcc ccg gcc agc atg gtg ggc ggg aag         1981
Thr Glu Ser Ile Thr Ala Thr Ser Pro Ala Ser Met Val Gly Gly Lys
305                 310                 315                 320 cca ggc tcc ttc cgt gtc cgc gcc tcc agt gac ggc gaa ggc acc atg         2029
Pro Gly Ser Phe Arg Val Arg Ala Ser Ser Asp Gly Glu Gly Thr Met
                325                 330                 335 tcc cgc cca gcc tcg gtg gac ggc agc cct gtg agt ccc agc acc aac         2077
Ser Arg Pro Ala Ser Val Asp Gly Ser Pro Val Ser Pro Ser Thr Asn
        340                 345                 350 aga acc cac gcc cac cgg cat cgg ggc agc gcc cgg ctg cac ccc ccg         2125
Arg Thr His Ala His Arg His Arg Gly Ser Ala Arg Leu His Pro Pro
        355                 360                 365 ctc aac cac agc cgc tcc atc ccc atg ccg gct tcc cgc tgc tcg cct         2173
Leu Asn His Ser Arg Ser Ile Pro Met Pro Ala Ser Arg Cys Ser Pro
370                 375                 380 tcg gcc acc agc ccg gtc agt ctg tcg tcc agt agc acc agt ggc cat         2221
Ser Ala Thr Ser Pro Val Ser Leu Ser Ser Ser Ser Thr Ser Gly His
385                 390                 395                 400 ggc tcc acc tcg gat tgt ctc ttc cca cgg cga tct agt gct tcg gtg         2269
Gly Ser Thr Ser Asp Cys Leu Phe Pro Arg Arg Ser Ser Ala Ser Val
                405                 410                 415 tct ggt tcc ccc agc gat ggc ggt ttc atc tcc tcg gat gag tat ggc         2317
Ser Gly Ser Pro Ser Asp Gly Gly Phe Ile Ser Ser Asp Glu Tyr Gly
                420                 425                 430 tcc agt ccc tgc gat ttc cgg agt tcc ttc cgc agt gtc act ccg gat         2365
Ser Ser Pro Cys Asp Phe Arg Ser Ser Phe Arg Ser Val Thr Pro Asp
        435                 440                 445 tcc ctg ggc cac acc cca cca gcc cgc ggt gag gag gag cta agc aac         2413
Ser Leu Gly His Thr Pro Pro Ala Arg Gly Glu Glu Glu Leu Ser Asn
        450                 455                 460 tat atc tgc atg ggt ggc aag ggg ccc tcc acc ctg acc gcc ccc aac         2461
Tyr Ile Cys Met Gly Gly Lys Gly Pro Ser Thr Leu Thr Ala Pro Asn
465                 470                 475                 480 ggt cac tac att ttg tct cgg ggt ggc aat ggc cac cgc tgc acc cca         2509
Gly His Tyr Ile Leu Ser Arg Gly Gly Asn Gly His Arg Cys Thr Pro
                485                 490                 495 gga aca ggc ttg ggc acg agt cca gcc ttg gct ggg gat gaa gca gcc         2557
Gly Thr Gly Leu Gly Thr Ser Pro Ala Leu Ala Gly Asp Glu Ala Ala
                500                 505                 510 agt gct gca gat ctg gat aat cgg ttc cga aag aga act cac tcg gca         2605
Ser Ala Ala Asp Leu Asp Asn Arg Phe Arg Lys Arg Thr His Ser Ala
        515                 520                 525 ggc aca tcc cct acc att acc cac cag aag acc ccg tcc cag tcc tca         2653
Gly Thr Ser Pro Thr Ile Thr His Gln Lys Thr Pro Ser Gln Ser Ser
        530                 535                 540 gtg gct tcc att gag gag tac aca gag atg atg cct gcc tac cca cca         2701
Val Ala Ser Ile Glu Glu Tyr Thr Glu Met Met Pro Ala Tyr Pro Pro
545                 550                 555                 560 gga ggt ggc agt gga ggc cga ctg ccg gga cac agg cac tcc gcc ttc         2749
Gly Gly Gly Ser Gly Gly Arg Leu Pro Gly His Arg His Ser Ala Phe
                565                 570                 575 gtg ccc acc cgc tcc tac cca gag gag ggt ctg gaa atg cac ccc ttg         2797
Val Pro Thr Arg Ser Tyr Pro Glu Glu Gly Leu Glu Met His Pro Leu
        580                 585                 590
```

| | | |
|---|---|---|
| gag cgt cgg ggg ggg cac cac cgc cca gac agc tcc acc ctc cac acg<br>Glu Arg Arg Gly Gly His His Arg Pro Asp Ser Ser Thr Leu His Thr<br>     595                            600                      605 | 2845 |
| gat gat ggc tac atg ccc atg tcc cca ggg gtg gcc cca gtg ccc agt<br>Asp Asp Gly Tyr Met Pro Met Ser Pro Gly Val Ala Pro Val Pro Ser<br>610                            615                      620 | 2893 |
| ggc cga aag ggc agt gga gac tat atg ccc atg agc ccc aag agc gta<br>Gly Arg Lys Gly Ser Gly Asp Tyr Met Pro Met Ser Pro Lys Ser Val<br>625                            630                       635                      640 | 2941 |
| tct gcc cca cag cag atc atc aat ccc atc aga cgc cat ccc cag aga<br>Ser Ala Pro Gln Gln Ile Ile Asn Pro Ile Arg Arg His Pro Gln Arg<br>                        645                      650                      655 | 2989 |
| gtg gac ccc aat ggc tac atg atg atg tcc ccc agc ggt ggc tgc tct<br>Val Asp Pro Asn Gly Tyr Met Met Met Ser Pro Ser Gly Gly Cys Ser<br>                       660                       665                      670 | 3037 |
| cct gac att gga ggt ggc ccc agc agc agc agc agc agc aac gcc<br>Pro Asp Ile Gly Gly Gly Pro Ser Ser Ser Ser Ser Ser Asn Ala<br>675                            680                       685 | 3085 |
| gtc cct tcc ggg acc agc tat gga aag ctg tgg aca aac ggg gta ggg<br>Val Pro Ser Gly Thr Ser Tyr Gly Lys Leu Trp Thr Asn Gly Val Gly<br>         690                      695                      700 | 3133 |
| ggc cac cac tct cat gtc ttg cct cac ccc aaa ccc cca gtg gag agc<br>Gly His His Ser His Val Leu Pro His Pro Lys Pro Pro Val Glu Ser<br>705                            710                      715                      720 | 3181 |
| agc ggt ggt aag ctc tta cct tgc aca ggt gac tac atg aac atg tca<br>Ser Gly Gly Lys Leu Leu Pro Cys Thr Gly Asp Tyr Met Asn Met Ser<br>                       725                       730                      735 | 3229 |
| cca gtg ggg gac tcc aac acc agc agc ccc tcc gac tgc tac tac ggc<br>Pro Val Gly Asp Ser Asn Thr Ser Ser Pro Ser Asp Cys Tyr Tyr Gly<br>                      740                       745                      750 | 3277 |
| cct gag gac ccc cag cac aag cca gtc ctc tcc tac tac tca ttg cca<br>Pro Glu Asp Pro Gln His Lys Pro Val Leu Ser Tyr Tyr Ser Leu Pro<br>                   755                      760                      765 | 3325 |
| aga tcc ttt aag cac acc cag cgc ccc ggg gag ccg gag gag ggt gcc<br>Arg Ser Phe Lys His Thr Gln Arg Pro Gly Glu Pro Glu Glu Gly Ala<br>770                            775                      780 | 3373 |
| cgg cat cag cac ctc cgc ctt tcc act agc tct ggt cgc ctt ctc tat<br>Arg His Gln His Leu Arg Leu Ser Thr Ser Ser Gly Arg Leu Leu Tyr<br>785                            790                      795                      800 | 3421 |
| gct gca aca gca gat gat tct tcc tct tcc acc agc agc gac agc ctg<br>Ala Ala Thr Ala Asp Asp Ser Ser Ser Ser Thr Ser Ser Asp Ser Leu<br>                      805                       810                      815 | 3469 |
| ggt ggg gga tac tgc ggg gct agg ctg gag ccc agc ctt cca cat ccc<br>Gly Gly Gly Tyr Cys Gly Ala Arg Leu Glu Pro Ser Leu Pro His Pro<br>                   820                      825                      830 | 3517 |
| cac cat cag gtt ctg cag ccc cat ctg cct cga aag gtg gac aca gct<br>His His Gln Val Leu Gln Pro His Leu Pro Arg Lys Val Asp Thr Ala<br>835                            840                      845 | 3565 |
| gct cag acc aat agc cgc ctg gcc cgg ccc acg agg ctg tcc ctg ggg<br>Ala Gln Thr Asn Ser Arg Leu Ala Arg Pro Thr Arg Leu Ser Leu Gly<br>                      850                      855                      860 | 3613 |
| gat ccc aag gcc agc acc tta cct cgg gcc cga gag cag cag cag cag<br>Asp Pro Lys Ala Ser Thr Leu Pro Arg Ala Arg Glu Gln Gln Gln Gln<br>865                            870                      875                      880 | 3661 |
| cag cag ccc ttg ctg cac cct cca gag ccc aag agc ccg ggg gaa tat<br>Gln Gln Pro Leu Leu His Pro Pro Glu Pro Lys Ser Pro Gly Glu Tyr<br>                        885                      890                      895 | 3709 |
| gtc aat att gaa ttt ggg agt gat cag tct ggc tac ttg tct ggc ccg<br>Val Asn Ile Glu Phe Gly Ser Asp Gln Ser Gly Tyr Leu Ser Gly Pro<br>                   900                      905                      910 | 3757 |

```
gtg gct ttc cac agc tca cct tct gtc agg tgt cca tcc cag ctc cag    3805
Val Ala Phe His Ser Ser Pro Ser Val Arg Cys Pro Ser Gln Leu Gln
            915                 920                 925 cca gct ccc aga gag gaa gag act ggc act gag gag tac atg aag atg    3853
Pro Ala Pro Arg Glu Glu Glu Thr Gly Thr Glu Glu Tyr Met Lys Met
        930                 935                 940 gac ctg ggg ccg ggc cgg agg gca gcc tgg cag gag agc act ggg gtc    3901
Asp Leu Gly Pro Gly Arg Arg Ala Ala Trp Gln Glu Ser Thr Gly Val
945                 950                 955                 960 gag atg ggc aga ctg ggc cct gca cct ccc ggg gct gct agc att tgc    3949
Glu Met Gly Arg Leu Gly Pro Ala Pro Pro Gly Ala Ala Ser Ile Cys
                965                 970                 975 agg cct acc cgg gca gtg ccc agc agc cgg ggt gac tac atg acc atg    3997
Arg Pro Thr Arg Ala Val Pro Ser Ser Arg Gly Asp Tyr Met Thr Met
            980                 985                 990 cag atg agt tgt ccc cgt cag agc tac gtg gac acc tcg cca gct gcc    4045
Gln Met Ser Cys Pro Arg Gln Ser Tyr Val Asp Thr Ser Pro Ala Ala
        995                 1000                1005 cct gta agc tat gct gac atg cga aca ggc att gct gca gag gag gtg    4093
Pro Val Ser Tyr Ala Asp Met Arg Thr Gly Ile Ala Ala Glu Glu Val
    1010                1015                1020 agc ctg ccc agg gcc acc atg gct gct gcc tcc tca tcc tca gca gcc    4141
Ser Leu Pro Arg Ala Thr Met Ala Ala Ala Ser Ser Ser Ser Ala Ala
1025                1030                1035                1040 tct gct tcc ccg act ggg cct caa ggg gca gca gag ctg gct gcc cac    4189
Ser Ala Ser Pro Thr Gly Pro Gln Gly Ala Ala Glu Leu Ala Ala His
                1045                1050                1055 tcg tcc ctg ctg ggg ggc cca caa gga cct ggg ggc atg agc gcc ttc    4237
Ser Ser Leu Leu Gly Gly Pro Gln Gly Pro Gly Gly Met Ser Ala Phe
            1060                1065                1070 acc cgg gtg aac ctc agt cct aac cgc aac cag agt gcc aaa gtg atc    4285
Thr Arg Val Asn Leu Ser Pro Asn Arg Asn Gln Ser Ala Lys Val Ile
        1075                1080                1085 cgt gca gac cca caa ggg tgc cgg cgg agg cat agc tcc gag act ttc    4333
Arg Ala Asp Pro Gln Gly Cys Arg Arg Arg His Ser Ser Glu Thr Phe
    1090                1095                1100 tcc tca aca ccc agt gcc acc cgg gtg ggc aac aca gtg ccc ttt gga    4381
Ser Ser Thr Pro Ser Ala Thr Arg Val Gly Asn Thr Val Pro Phe Gly
1105                1110                1115                1120 gcg ggg gca gca gta ggg ggc ggt ggt agc agc agc agc agc gag    4429
Ala Gly Ala Ala Val Gly Gly Gly Gly Ser Ser Ser Ser Ser Glu
                1125                1130                1135 gat gtg aaa cgc cac agc tct gct tcc ttt gag aat gtg tgg ctg agg    4477
Asp Val Lys Arg His Ser Ser Ala Ser Phe Glu Asn Val Trp Leu Arg
            1140                1145                1150 cct ggg gag ctt ggg gga gcc ccc aag gag cca gcc aaa ctg tgt ggg    4525
Pro Gly Glu Leu Gly Gly Ala Pro Lys Glu Pro Ala Lys Leu Cys Gly
        1155                1160                1165 gct gct ggg ggt ttg gag aat ggt ctt aac tac ata gac ctg gat ttg    4573
Ala Ala Gly Gly Leu Glu Asn Gly Leu Asn Tyr Ile Asp Leu Asp Leu
    1170                1175                1180 gtc aag gac ttc aaa cag tgc cct cag gag tgc acc cct gaa ccg cag    4621
Val Lys Asp Phe Lys Gln Cys Pro Gln Glu Cys Thr Pro Glu Pro Gln
1185                1190                1195                1200 cct ccc cca ccc cca ccc cct cat caa ccc ctg ggc agc ggt gag agc    4669
Pro Pro Pro Pro Pro Pro Pro His Gln Pro Leu Gly Ser Gly Glu Ser
                1205                1210                1215 agc tcc acc cgc cgc tca agt gag gat tta agc gcc tat gcc agc atc    4717
Ser Ser Thr Arg Arg Ser Ser Glu Asp Leu Ser Ala Tyr Ala Ser Ile
```

```
                    1220            1225            1230
agt ttc cag aag cag cca gag gac cgt cag tagctcaact ggacatcaca      4767
Ser Phe Gln Lys Gln Pro Glu Asp Arg Gln
        1235            1240 gcagaatgaa gacctaaatg acctcagcaa atcctcttct aactcatggg tacccagact   4827
ctaaatattt catgattcac aactaggacc tcatatcttc ctcatcagta gatggtacga   4887
tgcatccatt tcagtttgtt tactttatcc aatcctcagg atttcattga ctgaactgca   4947
cgttctatat tgtgccaagc gaaaaaaaaa aatgcactgt gacaccagaa taatgagtct   5007
gcataaactt catcttcaac cttaaggact tagctggcca cagtgagctg atgtgcccac   5067
caccgtgtca tgagagaatg ggtttactct caatgcattt tcaagataca tttcatctgc   5127
tgctgaaact gtgtacgaca aagcatcatt gtaaattatt tcatacaaaa ctgttcacgt   5187
tgggtggaga gagtattaaa tatttaacat aggttttgat ttatatgtgt aattttttaa   5247
atgaaaatgt aacttttctt acagcacatc tttttttttgg atgtgggatg gaggtataca   5307
atgttctgtt gtaaagagtg gagcaaatgc ttaaaacaag gcttaaaaga gtagaatagg   5367
gtatgatcct tgttttaaga ttgtaattca gaaaacataa tataagaatc atagtgccat   5427
agatggttct caattgtata gttatatttg ctgatactat ctcttgtcat ataaacctga   5487
tgttgagctg agttccttat aagaattaat cttaattttg tattttttcc tgtaagacaa   5547
taggccatgt taattaaact gaagaaggat atatttggct gggtgttttc aaatgtcagc   5607
ttaaaattgg taattgaatg gaagcaaaat tataagaaga ggaaattaaa gtcttccatt   5667
gcatgtattg taaacagaag gagatggggtg attccttcaa ttcaaaagct ctctttggaa   5727
tgaacaatgt gggcgtttgt aaattctgga aatgtctttc tattcataat aaactagata   5787
ctgttgatct ttt                                                     5800
```

<210> SEQ ID NO 29
<211> LENGTH: 1242
<212> TYPE: PRT
<213> ORGANISM: Homo sapiens

<400> SEQUENCE: 29

```
Met Ala Ser Pro Pro Glu Ser Asp Gly Phe Ser Asp Val Arg Lys Val
1               5                   10                  15

Gly Tyr Leu Arg Lys Pro Lys Ser Met His Lys Arg Phe Phe Val Leu
            20                  25                  30

Arg Ala Ala Ser Glu Ala Gly Gly Pro Ala Arg Leu Glu Tyr Tyr Glu
        35                  40                  45

Asn Glu Lys Lys Trp Arg His Lys Ser Ser Ala Pro Lys Arg Ser Ile
    50                  55                  60

Pro Leu Glu Ser Cys Phe Asn Ile Asn Lys Arg Ala Asp Ser Lys Asn
65                  70                  75                  80

Lys His Leu Val Ala Leu Tyr Thr Arg Asp Glu His Phe Ala Ile Ala
                85                  90                  95

Ala Asp Ser Glu Ala Glu Gln Asp Ser Trp Tyr Gln Ala Leu Leu Gln
            100                 105                 110

Leu His Asn Arg Ala Lys Gly His His Asp Gly Ala Ala Ala Leu Gly
        115                 120                 125

Ala Gly Gly Gly Gly Ser Cys Ser Gly Ser Ser Gly Leu Gly Glu
    130                 135                 140

Ala Gly Glu Asp Leu Ser Tyr Gly Asp Val Pro Pro Gly Pro Ala Phe
145                 150                 155                 160
```

```
Lys Glu Val Trp Gln Val Ile Leu Lys Pro Lys Gly Leu Gly Gln Thr
            165                 170                 175

Lys Asn Leu Ile Gly Ile Tyr Arg Leu Cys Leu Thr Ser Lys Thr Ile
            180                 185                 190

Ser Phe Val Lys Leu Asn Ser Glu Ala Ala Val Val Leu Gln Leu
            195                 200                 205

Met Asn Ile Arg Arg Cys Gly His Ser Glu Asn Phe Phe Ile Glu
    210                 215                 220

Val Gly Arg Ser Ala Val Thr Gly Pro Gly Glu Phe Trp Met Gln Val
225                 230                 235                 240

Asp Asp Ser Val Val Ala Gln Asn Met His Glu Thr Ile Leu Glu Ala
                245                 250                 255

Met Arg Ala Met Ser Asp Glu Phe Arg Pro Arg Ser Lys Ser Gln Ser
                260                 265                 270

Ser Ser Asn Cys Ser Asn Pro Ile Ser Val Pro Leu Arg Arg His His
            275                 280                 285

Leu Asn Asn Pro Pro Ser Gln Val Gly Leu Thr Arg Arg Ser Arg
            290                 295                 300

Thr Glu Ser Ile Thr Ala Thr Ser Pro Ala Ser Met Val Gly Gly Lys
305                 310                 315                 320

Pro Gly Ser Phe Arg Val Arg Ala Ser Ser Asp Gly Glu Gly Thr Met
                325                 330                 335

Ser Arg Pro Ala Ser Val Asp Gly Ser Pro Val Ser Pro Ser Thr Asn
                340                 345                 350

Arg Thr His Ala His Arg His Arg Gly Ser Ala Arg Leu His Pro Pro
            355                 360                 365

Leu Asn His Ser Arg Ser Ile Pro Met Pro Ala Ser Arg Cys Ser Pro
            370                 375                 380

Ser Ala Thr Ser Pro Val Ser Leu Ser Ser Ser Thr Ser Gly His
385                 390                 395                 400

Gly Ser Thr Ser Asp Cys Leu Phe Pro Arg Arg Ser Ala Ser Val
                405                 410                 415

Ser Gly Ser Pro Ser Asp Gly Gly Phe Ile Ser Ser Asp Glu Tyr Gly
                420                 425                 430

Ser Ser Pro Cys Asp Phe Arg Ser Phe Arg Ser Val Thr Pro Asp
            435                 440                 445

Ser Leu Gly His Thr Pro Pro Ala Arg Gly Glu Glu Leu Ser Asn
450                 455                 460

Tyr Ile Cys Met Gly Gly Lys Gly Pro Ser Thr Leu Thr Ala Pro Asn
465                 470                 475                 480

Gly His Tyr Ile Leu Ser Arg Gly Gly Asn Gly His Arg Cys Thr Pro
                485                 490                 495

Gly Thr Gly Leu Gly Thr Ser Pro Ala Leu Ala Gly Asp Glu Ala Ala
            500                 505                 510

Ser Ala Ala Asp Leu Asp Asn Arg Phe Arg Lys Arg Thr His Ser Ala
            515                 520                 525

Gly Thr Ser Pro Thr Ile Thr His Gln Lys Thr Pro Ser Gln Ser Ser
            530                 535                 540

Val Ala Ser Ile Glu Glu Tyr Thr Glu Met Met Pro Ala Tyr Pro Pro
545                 550                 555                 560

Gly Gly Gly Ser Gly Gly Arg Leu Pro Gly His Arg His Ser Ala Phe
                565                 570                 575
```

```
Val Pro Thr Arg Ser Tyr Pro Glu Glu Gly Leu Glu Met His Pro Leu
            580                 585                 590

Glu Arg Arg Gly Gly His His Arg Pro Asp Ser Ser Thr Leu His Thr
        595                 600                 605

Asp Asp Gly Tyr Met Pro Met Ser Pro Gly Val Ala Pro Val Pro Ser
    610                 615                 620

Gly Arg Lys Gly Ser Gly Asp Tyr Met Pro Met Ser Pro Lys Ser Val
625                 630                 635                 640

Ser Ala Pro Gln Gln Ile Ile Asn Pro Ile Arg Arg His Pro Gln Arg
                645                 650                 655

Val Asp Pro Asn Gly Tyr Met Met Met Ser Pro Ser Gly Gly Cys Ser
            660                 665                 670

Pro Asp Ile Gly Gly Gly Pro Ser Ser Ser Ser Ser Ser Asn Ala
            675                 680                 685

Val Pro Ser Gly Thr Ser Tyr Gly Lys Leu Trp Thr Asn Gly Val Gly
        690                 695                 700

Gly His His Ser His Val Leu Pro His Pro Lys Pro Pro Val Glu Ser
705                 710                 715                 720

Ser Gly Gly Lys Leu Leu Pro Cys Thr Gly Asp Tyr Met Asn Met Ser
                725                 730                 735

Pro Val Gly Asp Ser Asn Thr Ser Ser Pro Ser Asp Cys Tyr Tyr Gly
            740                 745                 750

Pro Glu Asp Pro Gln His Lys Pro Val Leu Ser Tyr Tyr Ser Leu Pro
        755                 760                 765

Arg Ser Phe Lys His Thr Gln Arg Pro Gly Glu Pro Glu Glu Gly Ala
770                 775                 780

Arg His Gln His Leu Arg Leu Ser Thr Ser Ser Gly Arg Leu Leu Tyr
785                 790                 795                 800

Ala Ala Thr Ala Asp Asp Ser Ser Ser Thr Ser Ser Asp Ser Leu
            805                 810                 815

Gly Gly Gly Tyr Cys Gly Ala Arg Leu Glu Pro Ser Leu Pro His Pro
            820                 825                 830

His His Gln Val Leu Gln Pro His Leu Pro Arg Lys Val Asp Thr Ala
        835                 840                 845

Ala Gln Thr Asn Ser Arg Leu Ala Arg Pro Thr Arg Leu Ser Leu Gly
    850                 855                 860

Asp Pro Lys Ala Ser Thr Leu Pro Arg Ala Arg Glu Gln Gln Gln Gln
865                 870                 875                 880

Gln Gln Pro Leu Leu His Pro Pro Glu Pro Lys Ser Pro Gly Glu Tyr
                885                 890                 895

Val Asn Ile Glu Phe Gly Ser Asp Gln Ser Gly Tyr Leu Ser Gly Pro
            900                 905                 910

Val Ala Phe His Ser Ser Pro Ser Val Arg Cys Pro Ser Gln Leu Gln
        915                 920                 925

Pro Ala Pro Arg Glu Glu Glu Thr Gly Thr Glu Tyr Met Lys Met
    930                 935                 940

Asp Leu Gly Pro Gly Arg Arg Ala Ala Trp Gln Glu Ser Thr Gly Val
945                 950                 955                 960

Glu Met Gly Arg Leu Gly Pro Ala Pro Gly Ala Ala Ser Ile Cys
                965                 970                 975

Arg Pro Thr Arg Ala Val Pro Ser Ser Arg Gly Asp Tyr Met Thr Met
            980                 985                 990

Gln Met Ser Cys Pro Arg Gln Ser Tyr Val Asp Thr Ser Pro Ala Ala
```

```
                995              1000             1005
Pro Val Ser Tyr Ala Asp Met Arg Thr Gly Ile Ala Ala Glu Glu Val
        1010             1015             1020
Ser Leu Pro Arg Ala Thr Met Ala Ala Ala Ser Ser Ser Ser Ala Ala
1025             1030             1035             1040
Ser Ala Ser Pro Thr Gly Pro Gln Gly Ala Ala Glu Leu Ala Ala His
            1045             1050             1055
Ser Ser Leu Leu Gly Gly Pro Gln Gly Pro Gly Gly Met Ser Ala Phe
            1060             1065             1070
Thr Arg Val Asn Leu Ser Pro Asn Arg Asn Gln Ser Ala Lys Val Ile
        1075             1080             1085
Arg Ala Asp Pro Gln Gly Cys Arg Arg Arg His Ser Ser Glu Thr Phe
        1090             1095             1100
Ser Ser Thr Pro Ser Ala Thr Arg Val Gly Asn Thr Val Pro Phe Gly
1105             1110             1115             1120
Ala Gly Ala Ala Val Gly Gly Gly Gly Ser Ser Ser Ser Ser Ser Glu
            1125             1130             1135
Asp Val Lys Arg His Ser Ser Ala Ser Phe Glu Asn Val Trp Leu Arg
        1140             1145             1150
Pro Gly Glu Leu Gly Gly Ala Pro Lys Glu Pro Ala Lys Leu Cys Gly
        1155             1160             1165
Ala Ala Gly Gly Leu Glu Asn Gly Leu Asn Tyr Ile Asp Leu Asp Leu
    1170             1175             1180
Val Lys Asp Phe Lys Gln Cys Pro Gln Glu Cys Thr Pro Glu Pro Gln
1185             1190             1195             1200
Pro Pro Pro Pro Pro Pro His Gln Pro Leu Gly Ser Gly Glu Ser
            1205             1210             1215
Ser Ser Thr Arg Arg Ser Ser Glu Asp Leu Ser Ala Tyr Ala Ser Ile
        1220             1225             1230
Ser Phe Gln Lys Gln Pro Glu Asp Arg Gln
        1235             1240

<210> SEQ ID NO 30
<211> LENGTH: 14
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)
<223> OTHER INFORMATION: g, a, t or c

<400> SEQUENCE: 30
tttttttttt ttmn                                                    14
```

ANTISENSE OLIGONUCLEOTIDES CAPABLE OF INHIBITING THE FORMATION OF CAPILLARY TUBES BY ENDOTHELIAL CELLS

RELATED APPLICATIONS

This is a divisional of U.S. Ser. No. 10/735,512, filed Dec. 12, 2003, which is a continuation of International Application No. PCT/FR02/02067, with an international filing date of Jun. 14, 2002, which is based on French Patent Application No. 01/07805, filed Jun. 14, 2001.

TECHNICAL FIELD

I provide antisense oligonucleotides capable of inhibiting the expression of the protein IRS-1 and inhibiting the formation of capillary tubes by endothelial cells. Thus, my disclosure relates to antiangiogenic agents and anti-cell-multiplication agents, particularly, antitumor agents. The disclosure also pertains to pharmaceutical compositions containing said oligonucleotides and the use of said oligonucleotides as analysis reagents.

BACKGROUND

Angiogenesis is a fundamental process by means of which new blood vessels are formed. This process is essential in multiple normal physiological phenomena such as reproduction, development and even cicatrization. In these normal biological phenomena, angiogenesis is under strict control, i.e., it is triggered during a short period (several days) and then completely inhibited. However, many pathologies are linked to uncontrolled, invasive angiogenesis: arthritis, a pathology due to the damaging of cartilage by invasive neovessels; diabetic retinopathy or the invasion of the retina by neovessels leading to blindness of patients; neovascularization of the ocular apparatus which is a major cause of blindness. This neovascularization is involved in about twenty different eye diseases. Moreover, the growth and metastasis of tumors which are linked directly to neovascularization are dependent on angiogenesis. The tumor stimulates the growth of neovessels by its own growth. Moreover, these neovessels are escape routes for tumors which thereby join up with the blood circulation and induce metastases in sites remote from the initial tumor focus, such as the liver, lungs or bones.

Angiogenesis, the formation of neovessels by endothelial cells, involves the migration, growth and differentiation of endothelial cells. Regulation of these biological phenomena is directly linked to genetic expression.

SUMMARY

I provide a pharmaceutical composition that blocks angiogenesis including as active agent at least one substance selected from the group consisting of (i) a nucleic acid molecule of a gene coding for protein IRS-1, a complementary sequence or a fragment thereof and (ii) a molecule which inhibits expression of a nucleic acid molecule according to (i). I also provide a method of inhibiting angiogenesis including administering a pharmaceutically effective amount of the pharmaceutical composition.

I further provide a method of treating retinopathy, rheumatoid arthritis, Crohn's disease, atherosclerosis, hyperstimulation of the ovary, psoriasis, endometritis associated with neovascularization, restenosis due to balloon angioplasty, tissue superproduction due to cicatrization, peripheral vascular diseased, hypertension, vascular inflammation, Raynaud's disease and Raynaud's phenomena, aneurysm, arterial restenosis, thrombophlebitis, lymphangitis, lymphedema, tissue cicatrization and repair, ischemia, angina, myocardial infraction, chronic heart disease, congestive heart failure, age-related macular degeneration or osteoporosis including administering a pharmaceutically effective amount of the pharmaceutical composition.

I still further provide a method of diagnosing pathologies linked to angiogenesis including contacting a composition containing an active agent including at least one substance selected from the group consisting of (i) a nucleic acid molecule of a gene coding for protein IRS-1, a complementary sequence or a fragment thereof and (ii) a molecule which inhibits expression of a nucleic acid molecule according to (i) and target cells in a condition sufficient to permit inhibition of IRS-1 gene expression; measuring expression of the IRS-1 protein by the cells; and comparing expression of the protein measured before and after hybridization to measure inhibition of the expression.

BRIEF DESCRIPTION OF THE DRAWINGS

Other advantages and characteristics of my disclosure will become clear from the examples below in which the term "oligonucleotide" is used to designate the oligonucleotide of SEQ ID NO. 3 and which refer to the attached figures in which:

FIG. 3A shows the culture of untreated endothelial cells,

FIG. 3B shows the culture of endothelial cells stimulated with 3 ng/ml of bFGF,

FIG. 3C shows the culture of endothelial cells incubated with 100 µg/ml of oligonucleotide of SEQ ID NO. 3 for 4 hours and then stimulated with 3 ng/ml of bFGF, FIG. 3D shows the culture of endothelial cells incubated with 100 µg/ml of oligonucleotide of SEQ ID NO. 3 for 4 hours.

FIG. 4A shows the results obtained by subconjunctival injection of an antisense oligonucleotide at a concentration of 60 µm, FIG. 4B shows the results obtained after subconjunctival injection of a sense oligonucleotide at a concentration of 60 µm, FIG. 4C shows the results obtained after topical application of an antisense oligonucleotide at a concentration of 200 µm, FIG. 4D shows the results obtained after topical application of a sense oligonucleotide at a concentration of 200 µm, FIG. 4E illustrates the state of the cornea in the absence of any treatment, FIG. 4F illustrates the state of the cornea when treated with subconjunctival injections of PBS, FIGS. 5A to 5J illustrate the results of the inhibition of corneal neovascularization obtained in different groups of rats after de-epithelialization and limbic resection of the corneas of the rats on day 4 (FIGS. 5A to 5E) and on day 9 (FIGS. 5F to 5J). These are slit lamp photographs showing the comparison of the growth of the vessels in the various groups of rats. Enlargement×10.

DETAILED DESCRIPTION

Figure 1A:
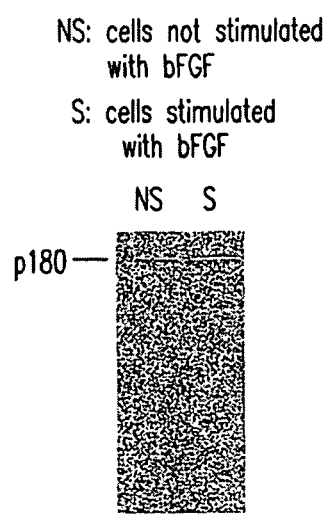
FIG. 1A is a Western Blot of images obtained from supernatant samples stemming from unstimulated cells (track NS) and cells stimulated with bFGF (track S) developed with an anti-IRS-1 antibody.

My work made it possible to identify and prepare nucleic acid sequences involved in the regulation of angiogenesis.

Other studies pertaining to angiogenesis have shown a noteworthy expression and phosphorylation at the level of a tyrosine residue of an intracellular 180-kDa protein by endothelial cells cultured on a surface of type I collagen and stimulated by an angiogenic factor such as bFGF. The noteworthy expression and phosphorylation at the level of the tyrosine residue of the intracellular 180-kDa protein accompanies the formation of capillary tubes by the endothelial cells.

That protein is already known as a substrate of the insulin receptor (called IRS-1). It has been partially identified and investigated by certain diabetes researchers (Quon et al., J. Biol. Chem. (1994), 269 (45), 27920-27924). Those authors studied the role of IRS-1 in (i) the translocation of GLUT 4 stimulated by insulin and (ii) the transport of glucose in rat adipose cells. In order to do this, they constructed a plasmid containing:

a double chain oligonucleotide obtained from the sense oligonucleotide of the following sequence SEQ ID NO. ID No. 1: 5'-TCGATGTGAC GCTACTGATG AGTC-CGTGAG GACGAAACTC TGGCCTAG-3' and cDNA coding for human IRS-1, and transfected rat adipose cells with said plasmid.

Our work revealed that the expression of the protein IRS-1 is also induced in endothelial cells when those cells are stimulated by the angiogenic factor bFGF.

My disclosure thus pertains to a pharmaceutical composition active on angiogenesis phenomena comprising as active agent at least one substance selected from among: (i) a nucleic acid molecule of the gene coding for the protein IRS-1, a complementary sequence or a fragment thereof, (ii) a molecule which inhibits the expression of a nucleic acid molecule according to (i).

Antisense oligonucleotides of the gene coding for this protein were prepared. These oligonucleotides have remarkable antiangiogenic and antitumor activities. They are therefore particularly useful in the treatment of diseases linked to invasive angiogenesis not controlled by gene therapy methods including administering to an individual a composition containing at least one of these oligonucleotides.

Thus, an oligonucleotide is constituted by the following nucleotide sequence of formula SEQ ID NO. 2:

5-TATCCGGAGGGCTCGCCATGCTGCTGCGGAGCAGA-3', a fragment thereof comprising at least 12 contiguous nucleotides or their derivative.

My disclosure pertains most particularly to an oligonucleotide constituted by one of the nucleotide sequences of formulas SEQ ID NO. 3 and 4 below:

5'-TATCCGGAGGGCTCGCCATGCTGCT-3',

5'-TCGCCATGCTGCTGCGGAGCAGA-3', a fragment of these comprising at least 12 contiguous nucleotides or their derivative.

The term "derivative" is understood to mean a sequence capable of hybridizing under strict conditions with one of the sequences SEQ ID NO. 2, 3 or 4, or with a fragment of these of at least 12 contiguous nucleotides.

The following sequences can be cited as non-limiting examples of oligonucleotides:

SEQ ID NO. 5:   5'-TATCCGGAGGGCCTGCCATGCTGCT-3',

SEQ ID NO. 6:   5'-TATCCGGAGG GCCTGCCATG CTGC-3',

SEQ ID NO. 7:   5'-TATCCGGAGG GCCTGCCATG CTG-3',

SEQ ID NO. 8:   5'-TATCCGGAGG GCCTGCCATG CT-3',

SEQ ID NO. 9:   5'-TATCCGGAGG GCCTGCCATG C-3',

SEQ ID NO. 10:  5'-TATCCGGAGG GCCTGCCATG-3',

SEQ ID NO. 11:  5'-TATCCGGAGG GCCTGCCAT-3',

SEQ ID NO. 12:  5'-TATCCGGAGG GCCTGCCA-3',

SEQ ID NO. 13:  5'-TATCCGGAGG GCCTGCC-3',

SEQ ID NO.14:   5'-TATCCGGAGG GCCTGC-3',

SEQ ID NO.15:   5'-TATCCGGAGG GCCTG-3',

SEQ ID NO.16:   5'-TATCCGGAGG GCCT-3',

SEQ ID NO.17:   5'-TATCCGGAGG GCC-3',

SEQ ID NO.18:   5'-TATCCGGAGG GC-3',

SEQ ID NO.19:   5'-CCGGAGG GCCTGCCATG CTGCT-3',

SEQ ID NO.20:   5'-GAGG GCCTGCCATG CTGCT-3',

SEQ ID NO.21:   5'-G GCCTGCCATG CTGCT-3',

SEQ ID NO.22:   5'-CTGCCATG CTGCT-3'.

SEQ ID NO.23:   5'-TGCCATG CTGCT-3'.

All or part of the phosphodiester bonds are advantageously protected. This protection is generally implemented via the chemical route using methods that are known by art. The phosphodiester bonds can be protected, for example, by a thiol or amine functional group or by a phenyl group.

The 5'- and/or 3'-ends of the oligonucleotides are also advantageously protected, for example, using the technique described above for protecting the phosphodiester bonds.

The oligonucleotides can be synthesized using conventional techniques that are known art, for example, using one of the DNA synthesizers marketed by various companies.

Although their mechanism of action has not been entirely elucidated, the oligonucleotides inhibit the expression of the protein IRS-1 within endothelial cells. These oligonucleotides block the formation of neovessels by endothelial cells (i.e., they inhibit angiogenesis) and thus they inhibit the multiplication of tumor cells in mice.

My disclosure therefore also includes a pharmaceutical composition that inhibits the gene coding for the protein IRS-1 comprising at least one oligonucleotide complementary of a part of said gene or of a transcript of said gene.

The molecule capable of inhibiting the expression of a nucleic acid molecule of the gene coding for the protein IRS-1 is preferably an antisense sequence of the region coding the sequence identified under the number SEQ ID NO. 28. The antisense sequence advantageously comprises at least twelve contiguous nucleotides or their derivative.

More preferentially, the active agent capable of inhibiting the expression of a nucleic acid molecule coding for the protein IRS-1 of the composition is a nucleotide sequence selected from SEQ ID NO. 2 to SEQ ID NO. 23 comprising at least twelve contiguous nucleotides or their derivative.

Such a composition advantageously comprises as an active agent at least one oligonucleotide as defined above advantageously combined in said composition with an acceptable vehicle.

My research made it possible to demonstrate that the protein IRS-1 represents a cellular constituent which is essential in the angiogenesis process. In fact, inhibition of the expression of the protein IRS-1 by said antisense oligonucleotides leads to the inhibition of the formation of capillary tubes by endothelial cells.

The oligonucleotides and the compositions containing them are thus antiangiogenic agents. They are also anti-cell-multiplication agents, particularly as antitumor agents, and consequently are particularly useful for the treatment of tumors. Thus, my disclosure includes the use of said oligonucleotides for the preparation of a composition intended for the treatment or prevention of pathologies linked to invasive, uncontrolled angiogenesis such as, as a nonlimitative example: the treatment of tumor vascularization, eye diseases linked to the neovascularization of the ocular apparatus such as retinopathies, rheumatoid arthritis, Crohn's disease, atherosclerosis, hyperstimulation of the ovary, psoriasis, endometritis associated with neovascularization, restenosis due to balloon angioplasty, tissue superproduction due to cicatrization, peripheral vascular disease, hypertension, vascular inflammation, Raynaud's disease and Raynaud's phenomena, aneurysm, arterial restenosis, thrombophlebitis, lymphangitis, lymphedema, tissue cicatrization and repair, ischemia, angina, myocardial infarction, chronic heart disease, cardiac insufficiencies such as congestive heart failure, age-related macular degeneration and osteoporosis.

The above pharmaceutical compositions are more particularly implemented in a manner such that they can be administered via the subcutaneous, intramuscular, intravenous or transdermal route, for example. For such administration, use is made of aqueous suspensions, isotonic saline solutions or sterile, injectable solutions containing pharmacologically compatible dispersion agents and/or wetting agents such as, for example, propylene glycol or butylene glycol.

The usual unit dose to be administered contains from about 0.001 mg to about 50 mg of active principle.

The oligonucleotides are also useful as research reagents, notably for the in vitro study of signalization routes involving the 180-kDa protein, for example, on tumor cells or non-tumor cells transfected by the oligonucleotides. They are also useful for the in vivo study of signalization routes involving the 180-kDa protein in a large number of physiological and pathological phenomena such as angiogenesis or carcinogenesis essentially from the kinase/phosphatase ratio.

Thus, the pharmaceutical compositions of my disclosure are particularly useful for the performance of tests for the diagnosis of pathologies linked to angiogenesis phenomena, notably for the diagnosis of retinopathies, rheumatoid arthritis, Crohn's disease, atherosclerosis, hyperstimulation of the ovary, psoriasis, endometritis association with neovascularization, restenosis due to balloon angioplasty, tissue superproduction due to cicatrization, peripheral vascular disease, hypertension, vascular inflammation, Raynaud's disease and Raynaud's phenomena, aneurysm, arterial restenosis, thrombophlebitis, lymphangitis, lymphedema, tissue cicatrization and repair, ischemia, angina, myocardial infarction, chronic heart disease, cardiac insufficiencies such as congestive heart failure or age-linked macular degeneration and osteoporosis.

My method of diagnosis comprises the follow steps:

contacting a composition containing an active agent including at least one substance selected from the group consisting of (i) a nucleic acid molecule of a gene coding for protein IRS-1, a complementary sequence or a fragment thereof and (ii) a molecule which inhibits expression of a nucleic acid molecule according to (i) and target cells in a condition sufficient to permit inhibition of IRS-1 gene expression;

measuring expression of the IRS-1 protein by the cells; and comparing expression of the protein measured before and after hybridization to measure inhibition of the expression.

The condition sufficient to permit inhibition of the IRS-1 gene expression are known in the art. Measuring the expression of the IRS-1 protein may be performed by techniques known in the art such as, for example, recognition by antibodies.

EXAMPLE 1

Demonstration of the Induction of the Expression of IRS-1 (the 180-kDa Protein) in Endothelial Cells Resulting from the Stimulation of these Cells with bFGF The 180-kDa protein was demonstrated in the following manner:

The endothelial cells were cultured in a 6-well microtitration plate previously covered with type I collagen as described in (Montesano et al., J. Cell. Biol., 1983, 83, 1648-1652). The culture medium was DMEM (Sigma) enriched with 10% of fetal calf serum, 4 mM glutamine, 500 U/ml penicillin and 100 µg/ml streptomycin. After 3 to 4 days of culture, there resulted a semi-confluent layer of endothelial cells. The culture medium of six wells was aspirated and replaced by fresh culture medium. Three wells were enriched with 3 ng/ml of bFGF. After incubation for 48 hours, the wells were washed three times with a phosphate buffer and the cells were used to extract the messenger RNA (mRNA) according to protocols known in the art. The mRNAs were reverse transcribed by a polymerization chain reaction (PCR) using each of four degenerated groups of oligo (dT) (T12MN) (SEQ ID No: 30) primers, M can be G, A or C; and N is G, A, T and C. Each group of primers is imposed by the base in position 3'(N) with a degeneration in the (M) position. Example: the set of primers in which N=G is constituted by:

SEQ ID NO. 24: 5'-TTTTTTTTTTTGG-3'

SEQ ID NO. 25: 5'-TTTTTTTTTTTAG-3'

SEQ ID NO. 26: 5'-TTTTTTTTTTTCG-3'

The cDNAs obtained in this manner were amplified and tagged by means of an arbitrary decamer in the presence of isotopically tagged ATP. The electrophoresis analysis of the cDNAs revealed the presence of an amplified 326-bp cDNA fragment in the sample stemming from the endothelial cells stimulated with bFGF, identified in the attached sequence listing as number SEQ ID NO. 27. However, this same fragment is weakly present or present in the trace state in the sample stemming from the endothelial cells that were not stimulated with bFGF. The sequencing of this fragment and the subsequent interrogation of the databases revealed that this fragment corresponds to a part of an already known gene, coding for the substrate of the insulin receptor (an intracellular 180-kDa protein).

EXAMPLE 2

Demonstration of the Induction of the Expression of IRS-1 The 180-kDa Protein

Figure 1B:
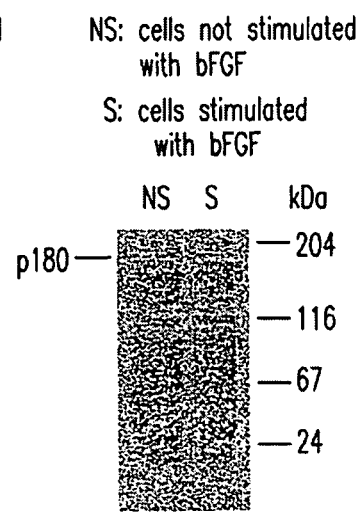
FIG. 1B is a Western Blot of images obtained after staining with silver nitrate obtained from the same supernatant samples stemming from unstimulated cells (track NS) and cells stimulated with bFGF (track S)

Endothelial cells cultured on a layer of type I collagen stimulated or not stimulated with bFGF (cf. example 1) were lysed in a cellular lyse buffer containing sodium orthovanadate. These solutions were then clarified by centrifugation at 14,000 g for 15 minutes. Supernatant samples stemming from unstimulated cells and cells stimulated with bFGF containing equivalent amounts of proteins were then taken up with an electrophoresis solution containing 2% SDS and 15 mM of dithiothreitol, heated at 100° C. for 5 minutes then deposited on polyacrylamide gel (gradient from 4 to 15% of acrylamide) under denatured conditions (in the presence of 2% SDS). After migration, the proteins were transferred onto a nitrocellulose membrane. The membrane was blocked by incubation at ambient temperature in a 5% milk solution in a PBS buffer. The membrane was then washed three times with a PBS buffer, incubated in a PBS buffer containing 1 µg/ml of anti-IRS-1 monoclonal antibody for 2 hours at ambient temperature and washed three times with a PBS buffer. The proteins were then developed with a secondary anti-isotope antibody coupled to peroxidase. The presence was noted of a protein of molecular weight 180 kDa recognized by the monoclonal anti-IRS-1 antibody in the preparations stemming from the endothelial cells stimulated with bFGF; this protein was weakly present in the preparation stemming from the endothelial cells not simulated with bFGF (FIG. 1).

EXAMPLE 3

Figure 2:
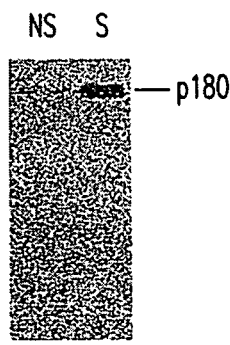
FIG. 2 is a Western Blot of images obtained from supernatant cells stemming from unstimulated cells (track NS) and cells stimulated with bFGF (track B) when the membrane is incubated with an anti-phosphotyrosine monoclonal antibody and developed with an anti-isotope antibody tagged at the peroxidase as indicated in Example 3.

Demonstration of the Induction of Phosphorylation at the Level of IRS-1 Tyrosine The 180-kDa Protein Human endothelial cells cultured on a layer of type I collagen stimulated or not stimulated with bFGF were lysed in a cellular lyse buffer containing sodium orthovanadate. These solutions were then clarified by centrifugation at 14,000 g for 15 minutes (cf. example 2). The IRS-1 protein was extracted by means of an anti-IRS-1 monoclonal antibody. This extraction was performed after immunoprecipitation by means of an anti-IRS-1 monoclonal antibody (Sigma). After addition of the anti-IRS-1 antibody coupled to agarose, the suspension was incubated for 2 hours at ambient temperature then centrifuged at 4000 g for 15 minutes. The resultant precipitate was taken up with an electrophoresis solution containing 2% SDS and 15 mM of dithiothreitol, heated at 100° C. for 5 minutes, then deposited on polyacrylamide gel (acrylamide gradient of 4 to 15%) under denaturing conditions (in the presence of 2% SDS). After migration, the proteins were transferred onto a nitrocellulose membrane. The membrane was blocked by incubation at ambient temperature in a 5% milk solution in a PBS buffer. The membrane was then washed three times with a PBS buffer, incubated in a PBS buffer containing 1 µg/ml of anti-phosphotyrosine monoclonal antibody for 2 hours at ambient temperature, and then washed three times with a PBS buffer. The proteins were then developed by means of a secondary anti-isotope antibody coupled to peroxidase. It was found that the IRS-1 protein of molecular weight 180 kDa was phosphorylated at the level of the tyrosine residue in the preparations stemming from the endothelial cells stimulated with bFGF; this protein was very weakly phosphorylated at the level of the tyrosine residue in the preparation stemming from the endothelial cells not stimulated with bFGF (FIG. 2).

EXAMPLE 4

Evaluation of the In Vitro Antiangiogenic Activity of the Oligonucleotide

Figure 3A:
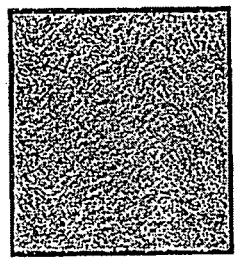
FIGS. 3A to 3D show the images of the cultures on a type I collagen surface of the different lots of endothelial cells.
Figure 3B:
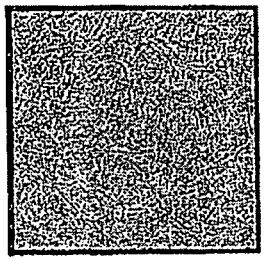
Figure 3C:
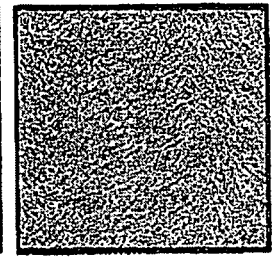
Figure 3D:
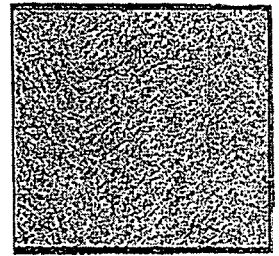
Figure 4A:
FIGS. 4A to 4F illustrate the results of tests of the inhibition of corneal neovascularization in rats.
Figure 4B:
Figure 4C:
Figure 4D:
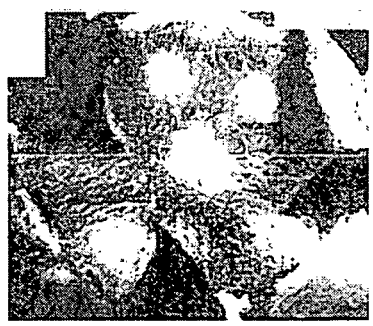
Figure 4E:
Figure 4F:

Human endothelial cells were cultured on a layer of type I collagen. The culture wells were divided into four lots on the seventh day of culture:
  Lot 1: Wells corresponding to the culture of untreated endothelial cells (FIG. 3A).
  Lot 2: Wells corresponding to the culture of endothelial cells stimulated with 3 ng/ml of bFGF (FIG. 3B).
  Lot 3: Wells corresponding to the culture of endothelial cells incubated with 100 µg/ml of oligonucleotide of SEQ ID NO. 3 for 4 hours then stimulated with 3 ng/ml of bFGF (FIG. 3C).
  Lot 4: Wells corresponding to the culture of endothelial cells incubated with 100 µg/ml of oligonucleotide of sequence SEQ ID NO. 3 for 4 hours (FIG. 3D).

The various wells were examined by means of an inverted phase optical microscope after 3 to 4 days of culture. Upon reading the results, it was found that the human endothelial cells in lot 2 formed capillary tubes following stimulation with bFGF. It was also found that the oligonucleotide inhibits the formation of neovessels by these same cells stimulated with bFGF in lot 3. Finally, it was found that that the oligonucleotide does not modify in a pronounced manner the growth of the endothelial cells. In fact, the numbers of endothelial cells in the lot 1 wells and in the lot 4 wells were comparable.

EXAMPLE 5

Evaluation of the In Vivo Activity of the Oligonucleotide

Three lots of naked mice were used. Each lot was constituted by 5 mice.
  Lot no. 1: This lot was used as control. Each mouse was inoculated on day 0 with 200 µl of a suspension of B16 melanoma cells (provided by Institut Gustave Roussy, Villejuif) dispersed in PBS at the level of $10^6$ cells/ml. These mice did not receive subsequent treatment.
  Lot no. 2: Each mouse was inoculated subcutaneously on day 0 with 200 µl of a suspension of B16 melanoma cells dispersed in PBS at the level of $10^6$ cells/ml. On day 1, day 2, day 3, day 4, day 5, day 6, day 7, day 8, day 9 and day 10 each mouse received a subcutaneous injection of 200 µl of an oligonucleotide solution diluted in PBS at a concentration of 500 µg/ml. The oligonucleotide injection was performed close to the cell injection site.
  Lot no. 3: The mice of this lot were not inoculated with the B16 melanoma cells. However, each of the mice received an injection of 200 µl of an oligonucleotide solution in PBS at a concentration of 500 µg/ml; the injections were performed on day 1, day 2, day 3, day 4, day 5, day 6, day 7, day 8, day 9 and day 10.

The following results were obtained:
In the mice of lot no. 1, the tumor mass developed very rapidly after inoculation. In fact, the tumor mass reached a size of 1.6 to 2.5 cm in diameter after ten days in the mice of said lot no. 1 (untreated mice). The evolution of the tumor mass in the mice of lot no. 2 (mice treated after inoculation by injection of oligonucleotide on day 1, day 2 and day 3), exhibited a clearly lower increase in the volume of the tumor mass. The tumor mass in the mice of lot 2 did not exceed 0.8 cm in diameter on the tenth day. On the fourteenth day, the difference between the tumor mass of the mice of lot no. 2 and those of lot no. 1 was remarkable.

In the mice of lot no. 3 (mice not having received B16 melanoma cells but treated by injection of oligonucleotide for three days), an unexpected general effect was observed on the skin. It was identical to that observed on all of the mice treated with the oligonucleotide (lot 2). The skin had an aged, crumpled appearance. The emergence of hairs was also observed on all of the treated mice. There was a parallelism during the evolution between the regression of the cutaneous signs and the resumption of tumor growth.

Thus, it was found that the oligonucleotide inhibits the development and formation of neovessels by endothelial cells in vitro. The oligonucleotide also has a remarkable in vivo antitumor activity in the naked mouse.

EXAMPLE 6

Evaluation of the Antiangiogenic Oligonucleotide on a Corneal Neovascularization Model in the Rat We employed, modified and analyzed a model of the formation of corneal neovessels in the rat after de-epithelialization and limbectomy (FIGS. 5A to 5J). It is reproducible, allows direct slit-lamp examination and quantification of the neovessels. The details are described below. The model was then used for testing the efficacy of the antiangiogenic agents.
Animals and corneal neovascularization model Male Wister rats (*Rattus norvegicus*), aged five weeks (Charles River France, St-Aubin les Elbeufs, France), free of specific pathogens, were fed and allowed to drink water freely, and maintained in the laboratory animal facility under fixed temperature and humidity conditions, with cycles of 12 hours of light/12 hours of darkness.

The rats were anesthetized with a mixture of ketamine (Kétamine 1000, UVA, Ivry-sur-Seine, France; 128 mg/kg) and chlorpromazine (Largactil 25 mg/ml; Specia Rhône Poulenc, Paris, France; 5 mg/kg), injected via the intramuscular route. A drop of oxybuprocaine (Novésine, Chibret, Clermont-Ferrand, France) was instilled in the right eye. Using an enlargement system (macroscope Wild MPS 51 S, LEICA, Heerbrugg, Switzerland), the corneal epithelium was removed by a microsponge impregnated with 70% ethanol. A 1.5-mm band of conjunctiva, at the limbus, was excised with microsurgical scissors, and the eyelids were closed by a temporary blepharorraphy with a Vicryl 5.0 thread (Dacron, Alcon, Rueil-Malmaison, France). The eye was then rinsed abundantly with 1×PBS, an oxytetracycline cream was applied (Posicycline, Alcon, France) and the blepharorraphy was opened on the fourth day [8, 9]. Treatment by subconjunctival injections and topical applications of antiangiogenic oligonucleotide The rats were divided into 6 groups:
Group A: model+subconjunctival injection of a 60-µM antisense oligonucleotide solution in 1×PBS,
Group B: model+topical application of a 200-µM antisense oligonucleotide solution in 1×PBS,
Group C: model+subconjunctival injection of a 60-µM sense oligonucleotide solution in 1×PBS,
Group D: model+topical application of a 200-1M sense oligonucleotide solution in 1×PBS,
Group E: model+subcutaneous injection of 1×PBS,
Group F: model without treatment.

All of the rats were subjected to de-epithelialization as described above; the treatment was performed every 24 hours starting on the fourth day and continuing until the ninth day. Neovascularization was examined at the beginning, in the middle and at the end of the protocol by slit-lamp examination; photographs were taken on day 0 and day 9.
Visualization and Quantification of the Neovascularization The animals were euthanized 10 days after the de-epithelialization by lethal injection of pentobarbital (intraperitoneal injection). In order to fill the microvessels and quantify the corneal neovascularization, the upper part of the animals' bodies were perfused with fluorescein-dextran 2×1,000,000. The eyes were enucleated and immersed in paraformaldehyde/1×PBS 4% for 3 hours, then overnight in 1×PBS. The cornea was then isolated with 1 mm of limbus under surgical microscope and inserted in the flat state between plate and cover by means of 3 to 5 radial incisions. The flat corneas were then examined and photographed using fluorescence microscopy. After the whole corneas were reconstituted, they were scanned and the surfaces were measured by image analysis; a software program (NIH image) was used for the quantification of the neovascularization. For each photo, the total corneal surface was measured three times as was the neovascularized surface; the ratio of the means—neovascularized surface/total corneal surface—was used to obtain the percentage of neovascularization and to measure the inhibition obtained.
Statistical Analysis The results were expressed as means ±SD. The percentages of neovascularized surface/total surface were compared with the nonparametric test of Mann-Whitney. Values of $P<0.05$ were considered to be significant.
Dilution of the Oligonucleotide The oligonucleotide was diluted in 1×PBS at pH 7.2. Based on the data in the literature and the experiments performed with other oligonucleotides, it was decided to use a concentration of 60 µM for the subconjunctival injections and a concentration of 200 µM for the topical applications.
Results Using the model of corneal neovessels, treatment was performed with the 5'-TATCCGGAGGGCTCGCCATGCTGCT-3' oligonucleotides identified under SEQ ID NO. 3 in the attached sequence listing modified in phosphorothioate form, daily, from day 4 to day 9, according to the following protocol:
Group A: subconjunctival injection of the antisense oligonucleotide at 60 µM (AS 60),
Group B: topical application of the antisense oligonucleotide at 200 µM (AS 200),
Group C: subconjunctival injection of the sense oligonucleotide at 60 µM (S 60),
Group D: topical application of the sense oligonucleotide at 200 µM (S 200),
Group E: subconjunctival injection of 1×PBS (PBS),
Group F: no treatment (0 Tt).

On the tenth day of the protocol, the rats were perfused with a solution of FITC/dextran and then euthanized. The corneas were collected and fixed in a 4% PAF solution. The corneas were then inserted in the flat state between plate and cover in a glycerol solution. The fluorescent neovessels were observed and photographed using the fluorescence microscope. The photographs were scanned and the neovascularization percentages were measured for each animal.

The results observed are presented in Table 1 below:

TABLE 1

|  | Group A AS 60 | Group B AS 200 | Group C S 60 | Group D S 200 | Group E PBS | Group F 0 Tt |
| --- | --- | --- | --- | --- | --- | --- |
| Mean | 0.6157 | 0.5058 | 0.9431 | 0.9392 | 0.9552 | 9.9170 |
| SD | 0.2194 | 0.1172 | 0.0964 | 0.0308 | 0.0481 | 0.0751 |
| Number of measurements | 15 | 15 | 15 | 12 | 9 | 9 |
| SEM | 0.0566 | 0.0303 | 0.0249 | 0.0089 | 0.0160 | 0.0250 |

The statistical analysis of the results using a nonparametric Mann-Whitney test yielded the following results:

The subconjunctival injections of 60-µM of the antisense oligonucleotide (A) reduced neovascularization in relation to the control groups E and F (very significant results, $P<0.0001$ and $P=0.0011$); topical application of the antisense oligonucleotide at a concentration of 200 µM (B) reduced neovascularization in relation to the control groups. E and F (extremely significant results, $P<0.0001$).

Compared to the subconjunctival administration of the sense oligonucleotide at 60 µM (C) or the topical application of the sense oligonucleotide at 200 µM (D), injection of the antisense oligonucleotide at 60 µM (A) and topical application of the antisense oligonucleotide at 200 µM (B) reduced neovascularization. These results were extremely significant ($P<0.0001$) (FIGS. 4A to 4F).

The inhibition of neovascularization was not significantly different depending on whether the antisense oligonucleotide was administered via the subconjunctival route (60 µM) or applied topically (200 µM). It was approximately 35% in relation to the controls (E and F).

The subconjunctival injection of the sense oligonucleotide at 60 µM (C) and the topical application of the sense oligonucleotide at a concentration of 200 µM (D) did not modify the neovascularization in relation to the control groups (E and F). In contrast, there was a small effect of the sense oligonucleotide in topical application (D) compared to the sense oligonucleotide in subconjunctival injections (C) ($P=0.0117$).

Moreover, there was seen in the groups treated with the antisense oligonucleotide (A and B), a smaller diameter and density of the neovessels. Their distribution did not differ in relation to the control groups nor was any difference observed in relation to the level of inflammation (FIG. 4).

Secondary Effects

No noteworthy secondary effects were seen in any of the groups during the two experimental series: after 6 days of treatment at the doses specified above, the skin of the rats was not crumpled, the fur was unchanged and the general condition of the animals was good; they fed normally until the last day and no suspicious mortality was observed. Although neither autopsies nor blood tests were performed, the general status of the animals at the end of the experiments did not suggest hepatic disorders. The only symptom observed was a transitory whitish deposit at the site of the conjunctival injections in 60% of the rats of group A, 60% of the rats of group C and 10% of the rats of group E. This deposit had been resorbed by the end of the experiments in all cases.

This example shows that—contrary to expectations—the subcutaneous injections of antisense oligonucleotide at a concentration of 60 µM did not inhibit neovascularization to a greater extent than the topical application of the antisense oligonucleotide at a concentration of 200 µM.

This can perhaps be explained by the difference in the concentrations employed; but this results suggests also a penetration of the oligonucleotide via the topical route rather than via the limbus. It also suggests the absence of prolonged release of the product from the injection site.

CONCLUSION

The application of the antisense oligonucleotide via the topical route or in subconjunctival injections reduces neovascularization in our model of corneal neovessels in the rat.

The purpose of this study was to test the efficacy of the antisense oligonucleotides stemming from the sequence of the gene IRS-1 on a previously developed model of corneal neovascularization in the rat.

BIBLIOGRAPHY

1. Aiello L P. Keeping in touch with angiogenesis. *Nat Med* 2000; 6: 379-381.

2. D'Amore P A. Mechanisms of Retinal and Choroidal Neovascularization. *Invest Ophthalmol Vis Sci* 1994; 35(12): 3974-3979.

3. Hélène C. Rational design of sequence-specific oncogene inhibitors based on antisense and antigene oligonucleotides. *Eur J Cancer* 1991; 27: 1466-1471.

4. Agrawal S, Bunnel B A, Crooke S T, Davidkova G, Gyurko R, Iyer K et al. Antisense oligonucleotides and antisense RNA. Benjamin Weiss edition (Philadelphia, USA) 1997; 1-11, 19-40.

5. Pierga J Y, Cammilleri S, Benyahia B, Magdelénat H. Applications of antisense oligonucleotides in cancer research. *Bull Cancer* 1994; 81: 1023-1042.

6. Robinson G S, Pierce E A, Rook S L, Foley E, Webb R, Smith L E H. Oligodeoxynucleotides inhibit retinal neovascularization in a murine model of proliferative retinopathy. *Proc Natl Acad Sci USA* 1996; 93: 4851-4856.

7. Aiello L P. Vascular endothelial growth factor. *Invest Opthalmol Vis Sci* 1997; 38: 1647-1652.

8. Amano S, Rohan R, Kuroki M, Tolentino M, Adamis A P. Requirement for vascular endothelial growth factor in wound and inflammation-related corneal neovascularization. *Invest Opthalmol Vis Sci* 1998; 39: 18-22.

9. Hoang-Xuan T, Prisant O. Restoration of corneal epithelium from limbic stem cells. *Med Sci* 1998; 14: 1375-1377.

10. Parry T J, Cushman C, Gallegos A M, Agrawal A B, Richardson M, Andres L E et al. Bioactivity of antiangiogenic ribozymes targeting Flt-1 and KDR mRNA. *Nucleic Acids Research* 1999; 27: 2569-2577.

11. Ozaki H, Seo M S, Ozaki K, Yamada H, Yamada E, Okamoto N et al. Blockade of vascular endothelial cell growth factor receptor signaling is sufficient to completely prevent retinal neovascularization. *Am J Pathol* 2000; 156: 697-707.

12. Berdugo Polak M. Iontophoresis administration of antisense oligonucleotides in the anterior segment of the eye: application to a corneal neovascularization model in the rat. DEA "Biology and Pathology of the Epithelia"; University of Paris VII, Feldmann G; Inserm U450, Director Courtois Y, under the direction of Behar Cohen F. 2000.

The invention claimed is:

1. A method of inhibiting angiogenesis to treat diseases selected from the group consisting of rheumatoid arthritis, Crohn's disease, hyperstimulation of the ovary, endometritis associated with neovascularization, vascular inflammation, Raynaud's disease and Raynaud's phenomena, aneurysm, thrombophlebitis, lymphangitis, lymphedema, tissue cicatrization and repair, angina, age-related macular degeneration and osteoporosis comprising administering a pharmaceutically effective amount of a composition comprising at least one active molecule which inhibits expression of a nucleic acid molecule of a gene coding for protein IRS-1 selected from the group consisting of:

i) an antisense sequence of a coding region of SEQ ID NO. 28 comprising at least twelve contiguous nucleotides, and ii) SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, and fragments thereof comprising at least 12 contiguous nucleotides.

2. The method according to claim 1, wherein the composition contains an amount of the at least one active molecule that is about 0.001 mg to about 50 mg and the composition is in a form capable of subcutaneous, intramuscular, intravenous or transdermal administration.

3. A method of inhibiting angiogenesis to treat a disease selected from the group consisting of age-related macular degeneration and corneal neovascularization, comprising administering a pharmaceutically effective amount of a composition comprising at least one active molecule which inhibits expression of a nucleic acid molecule of a gene coding for protein IRS-1 selected from the group consisting of:
  i) an antisense sequence of a coding region of SEQ ID NO. 28comprising at least twelve contiguous nucleotides, and
  ii) SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, and fragments thereof comprising at least 12 contiguous nucleotides.

4. The method according to claim 3, wherein the composition contains an amount of the at least one active molecule that is about 0.001 mg to about 50 mg and the composition is in a form capable of subcutaneous, intramuscular, intravenous or transdermal administration.

* * * * *